US012256959B2

(12) United States Patent
Forsberg

(10) Patent No.: US 12,256,959 B2
(45) Date of Patent: *Mar. 25, 2025

(54) ORTHOPAEDIC FIXATION ASSEMBLY, SYSTEM, AND METHOD OF USE

(71) Applicant: MT Innovations, LLC., Whitefish, MT (US)

(72) Inventor: Jonathan A. Forsberg, Kensington, MD (US)

(73) Assignee: MT Innovations, LLC., Whitefish, MT (US)

( * ) Notice: Subject to any disclaimer, the term of this patent is extended or adjusted under 35 U.S.C. 154(b) by 16 days.

This patent is subject to a terminal disclaimer.

(21) Appl. No.: 18/349,441

(22) Filed: Jul. 10, 2023

(65) Prior Publication Data

US 2023/0346430 A1 Nov. 2, 2023

Related U.S. Application Data

(63) Continuation of application No. 17/156,973, filed on Jan. 25, 2021, now Pat. No. 11,730,520, which is a
(Continued)

(51) Int. Cl.
*A61B 17/72* (2006.01)
*A61B 17/64* (2006.01)
(Continued)

(52) U.S. Cl.
CPC .......... *A61B 17/6425* (2013.01); *A61B 17/74* (2013.01); *A61F 2/78* (2013.01);
(Continued)

(58) Field of Classification Search
CPC . A61B 17/72; A61B 17/7216; A61B 17/7225; A61B 17/7233; A61B 17/7241;
(Continued)

(56) References Cited

U.S. PATENT DOCUMENTS 5,360,448 A * 11/1994 Thramann ............. A61L 31/146
606/76
6,869,450 B2 3/2005 Grundei
(Continued)

FOREIGN PATENT DOCUMENTS

WO 2009105535 A1 8/2009

OTHER PUBLICATIONS

Office Action issued on Apr. 5, 2023, in corresponding European Application No. 18844513.4, 6 pages.
(Continued)

*Primary Examiner* — Ellen C Hammond
*Assistant Examiner* — Christina Negrellirodriguez
(74) *Attorney, Agent, or Firm* — Maier & Maier, PLLC

(57) ABSTRACT

An orthopaedic fixation assembly for prosthetic biologic attachment. The orthopaedic fixation assembly may include a main body with a longitudinally-extending stem having a proximal end, a distal end, and a cavity body. An anchor plug may be configured to be received within the stem cavity, and securable thereto via complementary mating surfaces. A spindle structure may be fixedly attached to the proximal end of the longitudinally-extending stem and protrude outwardly therefrom such that a portion of the structure extends externally beyond the resected cavity of the bone that may prevent rotational motion of the spindle. The spindle structure may have at least one compliant biasing member configured to apply a compressive force to the surrounding bone. A porous coating may be at the juncture between stem and spindle structure, on the spindle, and the splines and anti-rotation chocks, improving the initial stability of the implant and facilitating long-term bone ingrowth.

18 Claims, 8 Drawing Sheets

Related U.S. Application Data continuation of application No. 16/051,732, filed on Aug. 1, 2018, now Pat. No. 10,952,774.

(60) Provisional application No. 62/541,896, filed on Aug. 7, 2017.

(51) Int. Cl.
| | | |
|---|---|---|
| *A61B 17/74* | (2006.01) | |
| *A61F 2/78* | (2006.01) | |
| *A61B 17/17* | (2006.01) | |
| *A61F 2/30* | (2006.01) | |
| *A61F 2/32* | (2006.01) | |
| *A61F 2/38* | (2006.01) | |
| *A61F 2/50* | (2006.01) | |

(52) U.S. Cl.
CPC ....... *A61B 17/1725* (2013.01); *A61B 17/1742* (2013.01); *A61B 17/72* (2013.01); *A61F 2/30767* (2013.01); *A61F 2/32* (2013.01); *A61F 2/389* (2013.01); *A61F 2002/5072* (2013.01); *A61F 2002/7887* (2013.01)

(58) Field of Classification Search
CPC .............. A61B 17/725; A61B 17/7258; A61B 17/7266; A61B 17/7275; A61B 17/7283
USPC ......................................... 606/60, 62–68, 95
See application file for complete search history.

(56) References Cited

U.S. PATENT DOCUMENTS

| | | | |
|---|---|---|---|
| 8,915,970 | B2 | 12/2014 | Porter et al. |
| 9,308,103 | B1 | 4/2016 | Kluger et al. |
| 11,730,520 | B2* | 8/2023 | Forsberg ................ A61B 17/74 |
| | | | 606/60 |
| 2006/0129247 | A1 | 6/2006 | Brown et al. |
| 2009/0048600 | A1* | 2/2009 | Matityahu .......... A61B 17/7241 |
| | | | 606/62 |
| 2009/0149964 | A1 | 6/2009 | May et al. |
| 2011/0160728 | A1 | 6/2011 | Blitz et al. |
| 2014/0214177 | A1 | 7/2014 | Porter et al. |
| 2015/0305897 | A1 | 10/2015 | Hershberger et al. |
| 2016/0100961 | A1 | 4/2016 | Porter et al. |

OTHER PUBLICATIONS

Examination Report issued on May 17, 2023, in corresponding Australian Application No. 2018313696, 5 pages.

European Search Report issued on Mar. 25, 2021, including the Supplementary European Search Report and the European Search Opinion, in connection with corresponding EP Application No. 18844513.4 (4 pp.).

Notification of Transmittal of the International Search Report and the Written Opinion of the International Searching Authority dated Nov. 19, 2018, in connection with corresponding International Application No. PCT/US18/44946 (11 pgs.).

\* cited by examiner

ORTHOPAEDIC FIXATION ASSEMBLY, SYSTEM, AND METHOD OF USE

CROSS-REFERENCE TO RELATED APPLICATIONS

This application is a Continuation of U.S. application Ser. No. 17/156,973, filed on Jan. 25, 2021, which claims priority from U.S. patent application Ser. No. 16/051,732, filed on Aug. 1, 2018 and U.S. Provisional Patent Application No. 62/541,896, filed on Aug. 7, 2017, entitled "Orthopaedic Fixation Assembly, System, and Method of Use," the entire contents of which are hereby incorporated by reference.

FIELD OF THE INVENTION

The present invention generally relates to an implantable prosthetic device, and more particularly, to an orthopaedic fixation device for in-bone implantation.

BACKGROUND

Despite their ability to withstand repeated loading forces, bones can deteriorate over time due to various diseases, injuries, and aging. Oncologic conditions, infectious diseases and trauma account for the majority of the 18,500 major limb amputations performed in the United States. Furthermore, nearly 20,000 limb-sparing and revision joint replacement surgeries are performed on patients with major bone deficits.

Various known orthopaedic fixation devices are used in the treatment of bone defects, amputations, and reconstructive surgeries. These devices create an interface between an artificial construct and bone. Under optimal circumstances, the interface should be able to withstand a variety of forces multiplied over several million expected cycles without breakdown. However, should breakdown occur, patients can experience significant local, and occasionally, systemic issues. Some fixation devices thus employ compliant mechanisms to support the prosthesis implantation, reducing bone loss and promoting bone ingrowth fixation.

SUMMARY

Exemplary embodiments described herein may relate generally to implantable prosthetic devices, and, more specifically, to an apparatus, system, and method for attaching prosthetic components to bone tissue. According to an exemplary embodiment, an orthopaedic fixation assembly for in-bone implantation may be provided. The orthopaedic fixation assembly may form a stabilization construct used for internal arthroplasty components, transdermal implant systems, and the like. The orthopaedic fixation assembly may include a main body adapted for insertion into a resected portion of the bone. The main body may include a longitudinally-extending stem having a proximal end, a distal end, and a cavity body defined therebetween. An anchor plug may be configured to be received within the stem cavity, and securable thereto via complementary mating surfaces. A spindle structure may be fixedly attached to the proximal end of the longitudinally-extending stem and protrude outwardly therefrom such that a portion of the structure extends externally beyond the resected cavity of the bone. The spindle structure may also house at least one compliant biasing member configured to apply a compressive force to the surrounding bone. A porous coating, interconnecting porous material, with or without osteoconductive coating, may be provided at the juncture between stem and spindle structure, as well as on anti-rotation chocks, improving an initial stability of the implant and facilitating long-term bone ingrowth.

In some exemplary embodiments, an internally-threaded end cap may be provided to secure the anchor plug within the stem cavity. The longitudinally-extending stem may have complementary external threads disposed on the distal end thereof to facilitate tightening of the end cap in place.

BRIEF DESCRIPTION OF THE DRAWINGS

Advantages of embodiments of the present invention will be apparent from the following detailed description of the exemplary embodiments. The following detailed description should be considered in conjunction with the accompanying figures in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

An orthopaedic fixation assembly for prosthetic biologic attachment may be described herein. The orthopaedic fixation assembly may be used in conjunction with internal arthroplasty components, transdermal implant systems, and the like for achieving osseointegration. The orthopaedic fixation assembly may provide the benefits of compliant pre-stress fixation with the rigidity and initial stability of a stemmed implant.

Figure 1A:
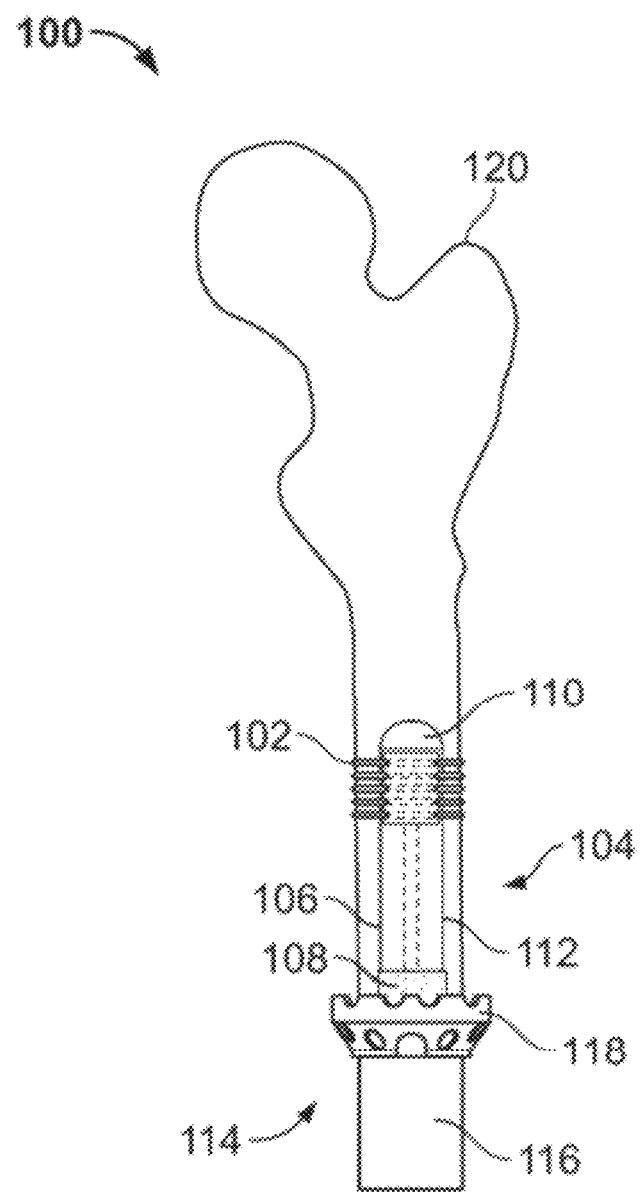
FIG. 1A is a cross-sectional view illustrating an exemplary embodiment of an orthopaedic fixation assembly implanted within a portion of a bone.

Referring now to the figures, and in particular to FIG. 1A, an exemplary embodiment of an implanted orthopaedic fixation assembly may be shown. The orthopaedic fixation assembly 100 may form a stabilization construct that provides a high-pressure bone-implant interface for biologic fixation or attachment and may be configured to be inserted into an intramedullary canal (not shown) of a bone 120. For illustrative purposes, FIG. 1A may show the implantation of the orthopaedic fixation assembly 100 within the bone 120 in an upper hind limb, such as a femur. As would be understood by a person having ordinary skill in the art, the orthopaedic fixation assembly 100 may be implanted within any other articulating bone, such as the humerus, pelvis, or tibia. Prior to implantation, a surgeon may make an incision to access and dislocate a joint, such as a hip, knee, ankle, shoulder, or elbow joint, exposing the articulating bone ends. Damaged or diseased cartilage and bone may then be removed, and the intramedullary canal prepared for receiving the orthopaedic fixation assembly 100. In particular, the intramedullary bone space may be carved out to create an enlarged canal having a predetermined depth and width relative to the osteotomy surface, as would be understood by a person having ordinary skill in the art. Additionally or alternatively, in the case of an amputation, the surgeon may make an incision to access the distal aspect of the humerus, pelvis, femur, or tibia. The orthopaedic fixation assembly 100 may then be inserted into the prepared intramedullary canal, and subsequently affixed or secured thereto via a plurality of transverse pins 102 or any other similar attachment or fixation devices, such as screws, pegs, barbs, wires, or anchors, as would be understood by a person having ordinary skill in the art.

The orthopaedic fixation assembly 100 may include a main body 104 adapted for insertion into the resected portion of the bone 120. The main body 104 may include a longitudinally-extending stem 106 having a proximal end 108, a distal end 110, and a cavity body 112 defined therebetween. A spindle structure 114 may be fixedly attached to the proximal end 108 of the longitudinally-extending stem 106, forming a unitary structure therewith. The spindle structure 114 may protrude outwardly from the stem 106, extending externally beyond the osteotomy surface. The spindle structure 114 may include a housing 116 having an annular flange 118 mounted thereto, the annular flange 118 configured to interface with the osteotomy surface. The annular flange 118 may thus engage a proximally-faced (or distally-faced, as desired) resected surface of, for example, the femoral, humeral, tibial diaphysis, or pelvic bone. The flange 118 may assist in maintaining and securing the orthopaedic fixation assembly 100 within the intramedullary canal and facilitate distribution of physiological forces, such as bending, shear, and rotational forces. The angle, size, and extent of the flange 118, for example, may depend on the anatomy of the patient and the morphology of the femoral, humeral, pelvic, or tibial resection level as would be understood by a person having ordinary skill in the art.

Figure 1B:
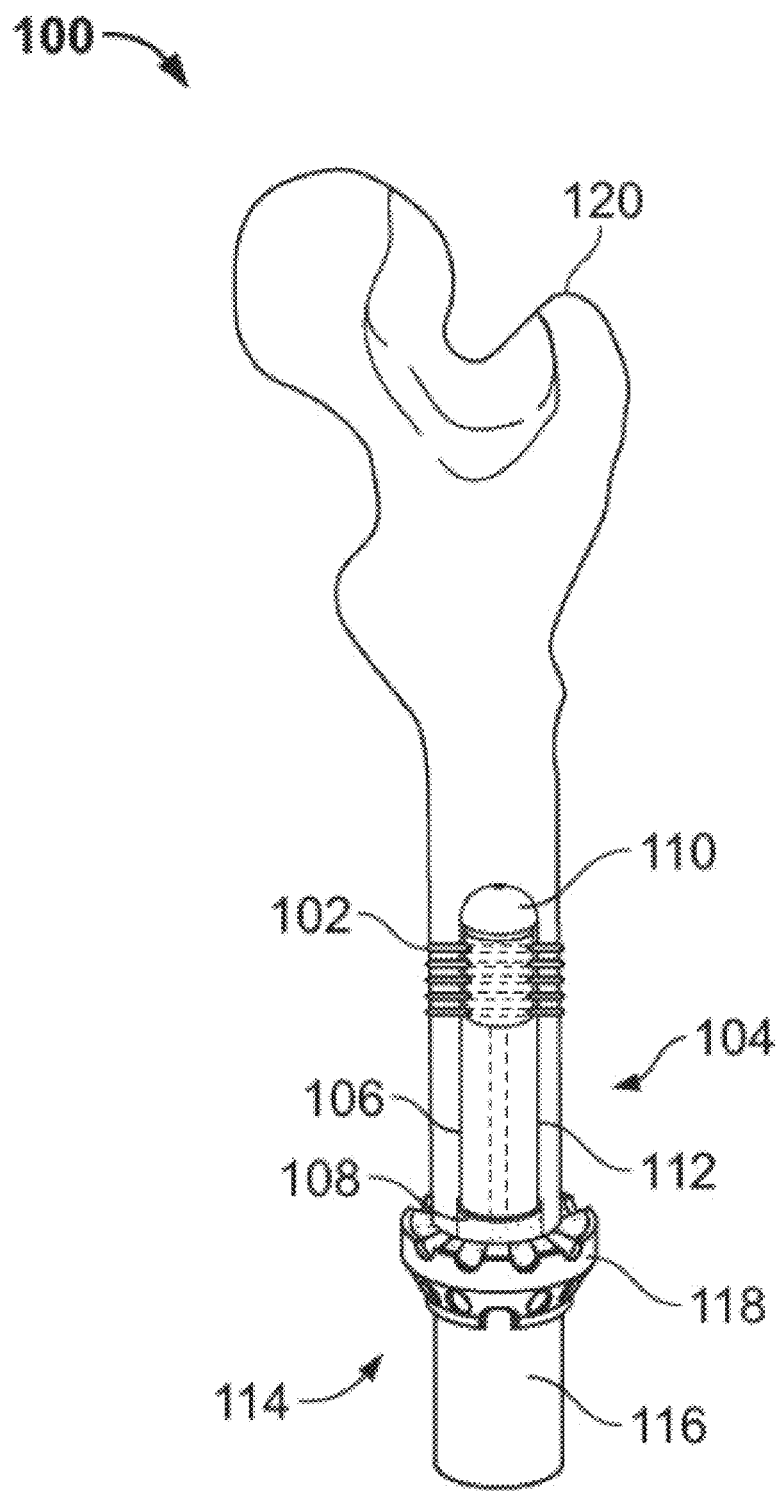
FIG. 1B is a cross-sectional view illustrating another exemplary embodiment of the orthopaedic fixation assembly implanted within a portion of a bone.

It should be appreciated that the orthopaedic fixation assembly 100 may be compatible with any bone structure for example, but not limited to, acetabulum, in patients with hip disarticulations, residual pelvic anatomy in patients with pelvic resections, or the distal radius in patients with wrist disarticulations. As shown in FIG. 1B, the orthopaedic fixation assembly 100 may vary in size and configuration, for example, to accommodate extremely short residual bones, such as those encountered in patients with amputations including, but not limited to, transhumeral, transfemoral, transtibial, hip disarticulation, or partial hemipelvectomy amputations.

Figure 2A:
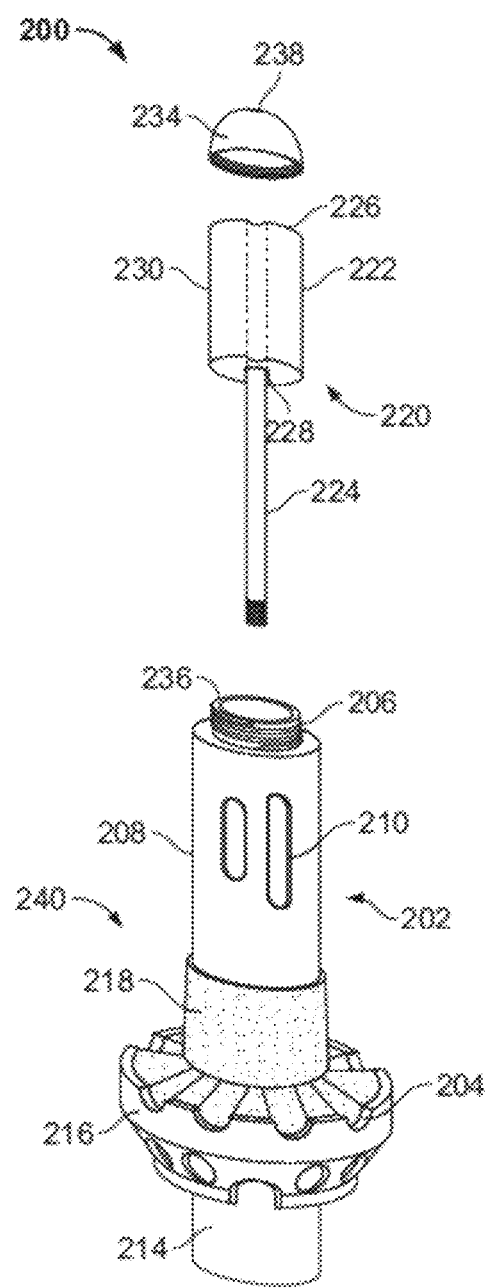
FIG. 2A is an exploded view illustrating a front perspective of an exemplary embodiment of the orthopaedic fixation assembly.
Figure 2B:
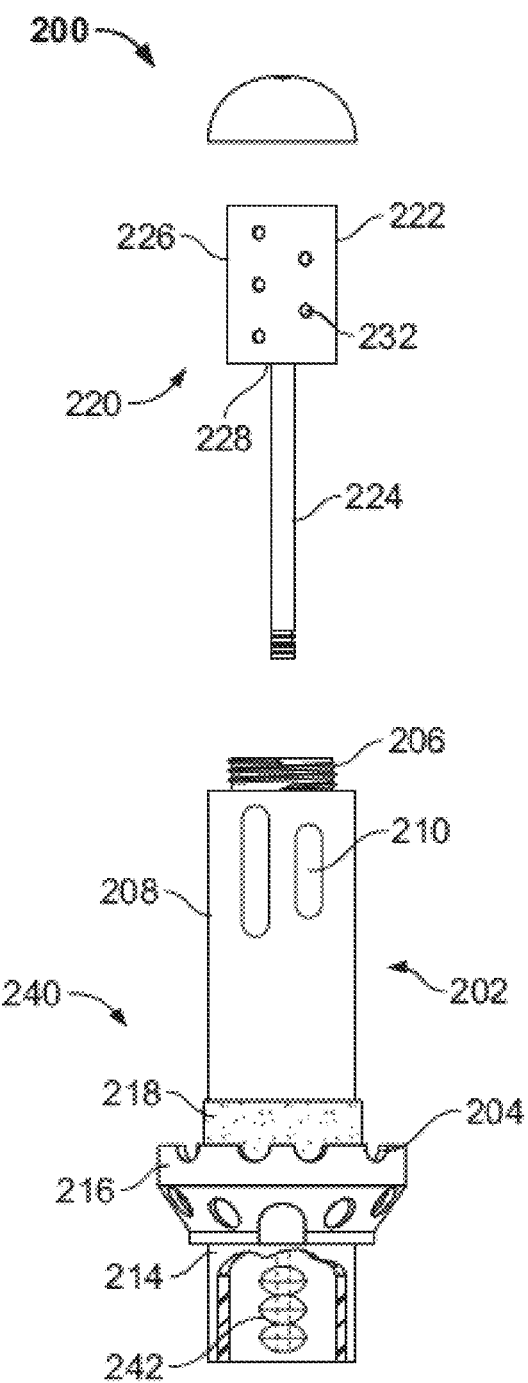
FIG. 2B is an exploded view illustrating a side perspective of the orthopaedic fixation assembly of FIG. 2A.

FIGS. 2A and 2B may depict an exploded view of an exemplary embodiment of the components of an orthopaedic fixation assembly 200 according to the present invention. The orthopaedic fixation assembly 200 may form a stabilization construct that provides a high-pressure bone-implant interface for biologic fixation or attachment. The orthopaedic fixation assembly 200 may include a main body 240 adapted for insertion into a resected portion of the bone 120, as shown in FIGS. 1A and 1B. The main body 240 may include a longitudinally-extending stem 202 having a proximal end 204, a distal end 206, and a cavity body 208 defined therebetween. The cavity body 208 may include one or more apertures 210 for receiving transverse fixation pins 102 (as shown in FIGS. 1A and 1B) or any other similar attachment or fixation devices, such as screws, pegs, barbs, wires, or anchors, therethrough. In some exemplary embodiments, and as shown in FIGS. 2A and 2B, the apertures 210 may take the form of elongated slots. As would be understood by a person having ordinary skill in the art, the apertures 210 may take the form of any other shape as may be desired. The apertures 210 may be arranged substantially parallel to one another, or may alternatively be configured in any suitable arrangement as would be understood by a person having ordinary skill in the art.

A spindle structure 212 may be fixedly attached to the proximal end 204 of the longitudinally-extending stem 202, and protrude outwardly therefrom, such that a portion of the structure extends externally beyond the resected cavity of the bone. The spindle structure 212 may include a housing 214 having an annular flange 216 mounted thereto, the annular flange 216 configured to interface with the osteotomy surface. The spindle structure 212 may also house at least one compliant biasing member 242, which may be Belleville washers in one exemplary embodiment, configured to apply a compressive force to the surrounding bone. The compliant biasing member may be disposed within an interior of the spindle structure 212, such that a bone biasing force is applied to at least a portion of the bone. The spindle structure 212 may be shaped and configured for accommodating the compliant member therein. The compliant biasing member 242 may generally form a structural member with enhanced compliance (i.e., greater elastic deformation when subjected to an applied force), such as a linear spring, coiled spring, bellow, Belleville washer, or any other elastic biasing member as would be understood by a person having ordinary skill in the art. In some exemplary embodiments, for example, the compliant biasing member 242 may include a Belleville washer having a fursto-conical shape and concentric aperture defined therethrough. In other exemplary embodiments, the compliant biasing member may include a plurality of conical washers stacked atop each other to form a Belleville spring. It should be appreciated that the compliant biasing member 242 may include any number, such as one or more, compliant biasing elements. The compliant biasing member 242 may provide a stable, high-pressure implant interface that allows osseointegration.

In addition, a porous coating 218, for example hydroxyapatite may be provided at the juncture between stem 202 and spindle structure 212, improving the stability and securement of the implant and facilitating long-term bone ingrowth. The coating may be applied to a roughened surface of the juncture region. The roughened surface may increase the surface area of the juncture, thereby improving adhesion of the coating. In addition, splines, or sharp longitudinal ridges, may be added to the coated juncture to provide further stability.

FIGS. 2A and 2B further illustrate an anchor plug 220 that may be received within the body cavity 208 of the stem 202 and securable thereto via complementary mating surfaces. The mating surfaces may be, for example, a tongue and groove locking mechanism that ensures the anchor plug 220 assumes the correct orientation within the body cavity 208, which will be described in greater detail below in FIGS. 3A and 3B. The anchor plug 220 may form a generally cylindrical body 222 having an elongated shaft 224 extending downwardly therefrom. For example, there may be male threads on the end of stem 206 that mate with end cap 234, although the male-female orientation may be reversed, as desired. The cylindrical body 222 may include a top portion 226, a bottom portion 228, and peripheral side wall 230 having a plurality of apertures 232 defined therein. Once the anchor plug 220 is inserted within the body cavity 208, the apertures 232 of the anchor plug 220 may align with the apertures 210 of the cavity body 208. For an orthopaedic fixation assembly that accommodates an extremely short residual bone, for example, the anchor plug 220 may not be contained entirely within the stem 202 itself.

In some exemplary embodiments, an internally-threaded end cap 234 may be provided to secure the anchor plug 220 within the body cavity 208 of the stem 202. The longitudinally-extending stem 202 may have complementary external threads 236 disposed on the distal end 206 thereof to facilitate tightening of the end cap 234 in place. A top portion 238 of the end cap 234 may have a female hex impression for engagement with a screwdriver or any other similar type of tool.

Figure 3A:
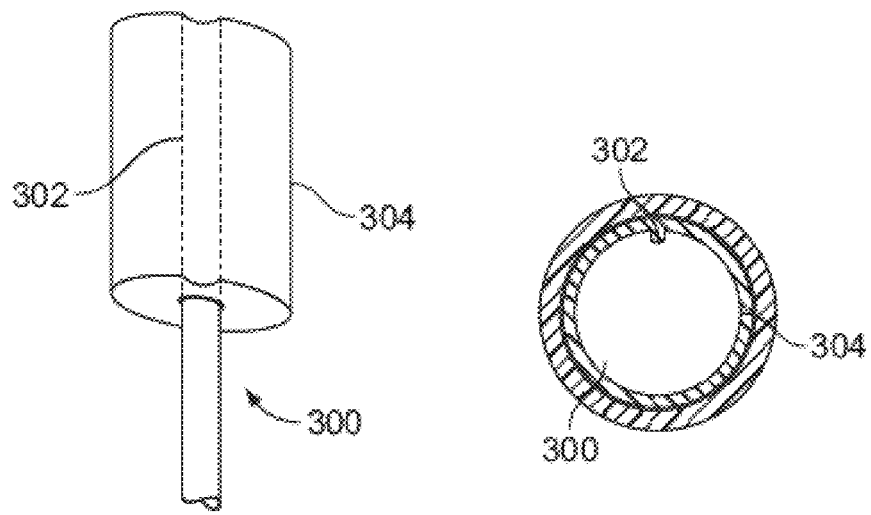
FIG. 3A is a perspective view illustrating an exemplary embodiment of an anchor plug.
Figure 3B:
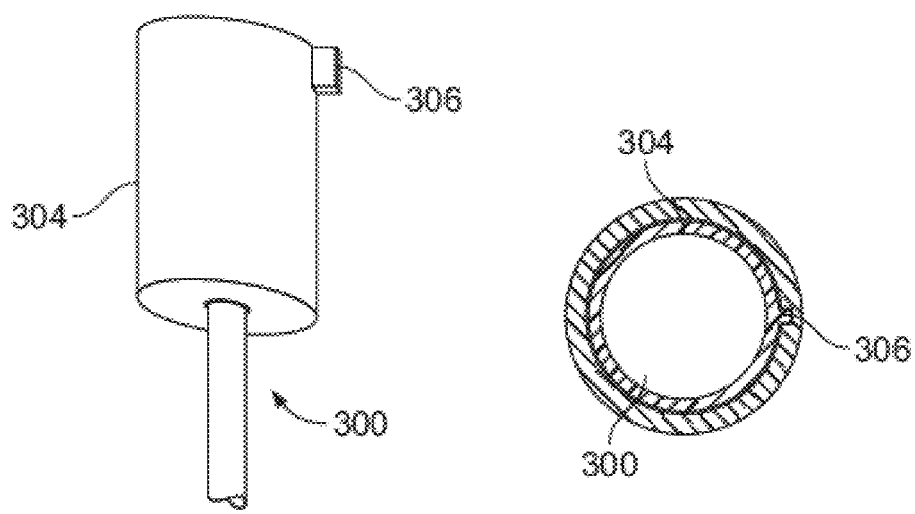
FIG. 3B is a perspective view illustrating another exemplary embodiment of the anchor plug.

FIGS. 3A and 3B may illustrate various orientations of the tongue and groove locking mechanism discussed above. As shown in FIG. 3A, for example, a groove 302 may extend along a length of a cylindrical body 304 of an anchor plug 300. The groove 302 may interface with a corresponding tongue component (not shown) disposed within the interior of the body cavity 208 of the stem 202, as illustrated in FIGS. 2A and 2B. Alternatively, as shown in FIG. 3B, a tongue or tab element 306 may extend along a length of the cylindrical body 304 of the anchor plug 300. The tongue 306 may interface with a corresponding groove (not shown) disposed within the interior of the body cavity 208 of the stem 202, as illustrated in FIGS. 2A and 2B. To accommodate certain deformities, or certain bones, such as the humerus, pelvis, femur, or tibia, the stem 202 (as shown in FIGS. 2A and 2B) and the anchor plug 300 may be elliptical or any other desired shape, as would be understood by a person having ordinary skill in the art, in which case, no groove 302 or tongue or tab element 306 may be necessary to ensure a correct and singular orientation of the anchor plug 300 within the body cavity 208 of the stem 202. This can ensure that cross-pins, screws, pegs, or anchors can be inserted using the targeting guide shown in exemplary FIG. 4.

Figure 4:
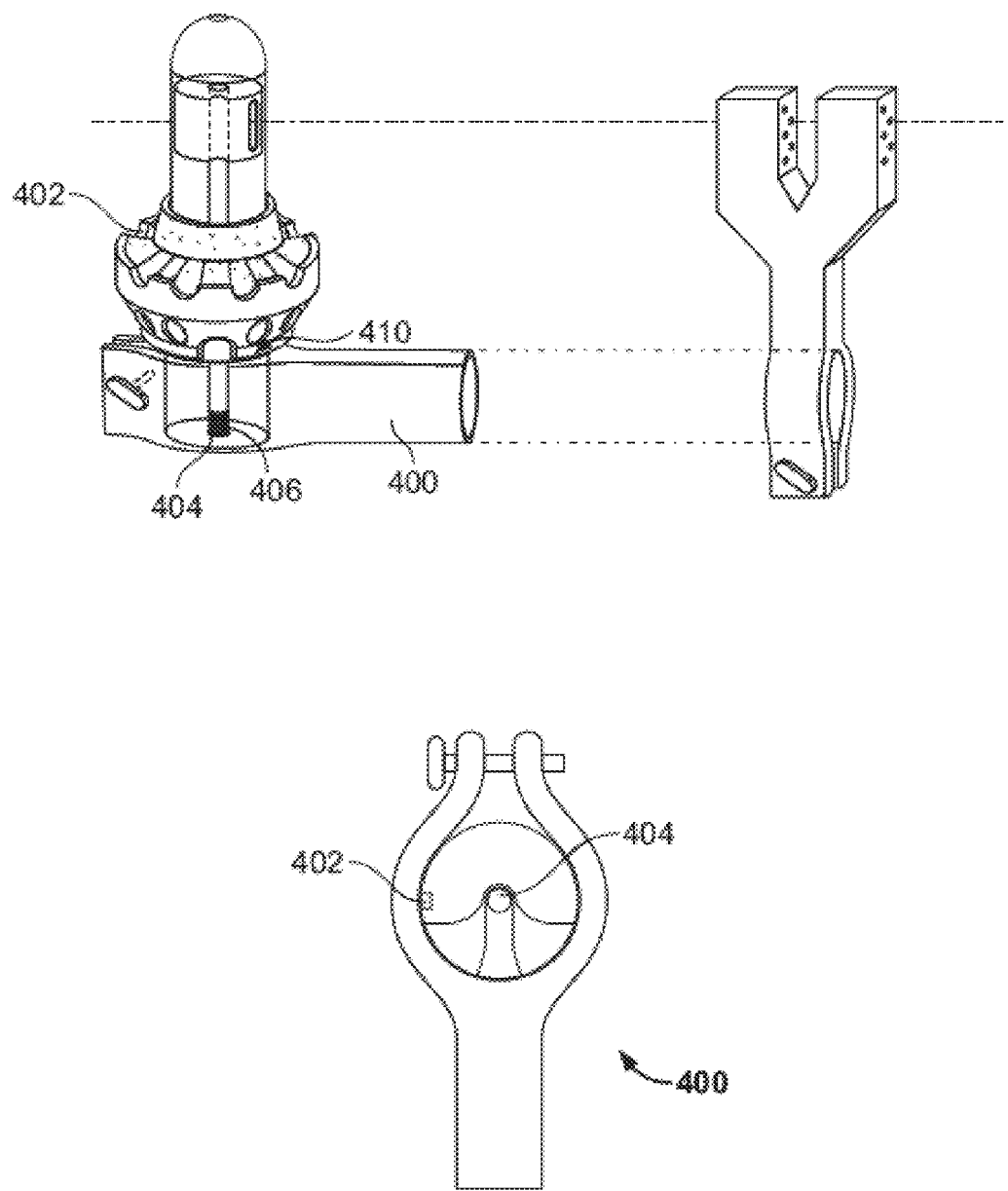
FIG. 4 is a perspective view illustrating an exemplary embodiment of a targeting guide for use in conjunction with the orthopaedic fixation assembly.

FIG. 4 may illustrate a perspective view of an exemplary embodiment of a targeting guide 400 for use in conjunction with an orthopaedic fixation assembly. The targeting guide 400 may fit over the spindle structure 410 and include alignment tabs 402 that ensure proper orientation and alignment of the targeting guide 400 and the spindle structure 410. The alignment tabs 402 may be disposed on a front and back of the spindle 410, for example at a 180-degree interval, so that a same orthopaedic fixation assembly and targeting guide 400 may be used to insert cross pins, screws, pegs, or anchors, in any orientation desired, regardless of the employed surgical exposure. Further, a pedestal 404 may be utilized to hold a traction bar 406 and attach anchor plug 220 in the correct orientation, so that transverse pins may be guided through corresponding apertures. The pedestal 404 may be manufactured onto the targeting guide 400, or, alternatively, may be fastened, screwed, snapped, or the like, into position. Targeting guide 400 may be utilized to drill holes in the bone and ensure accuracy when placing cross pins into the anchor plug, along with ensuring accuracy and desired performance and placement.

Figure 5:
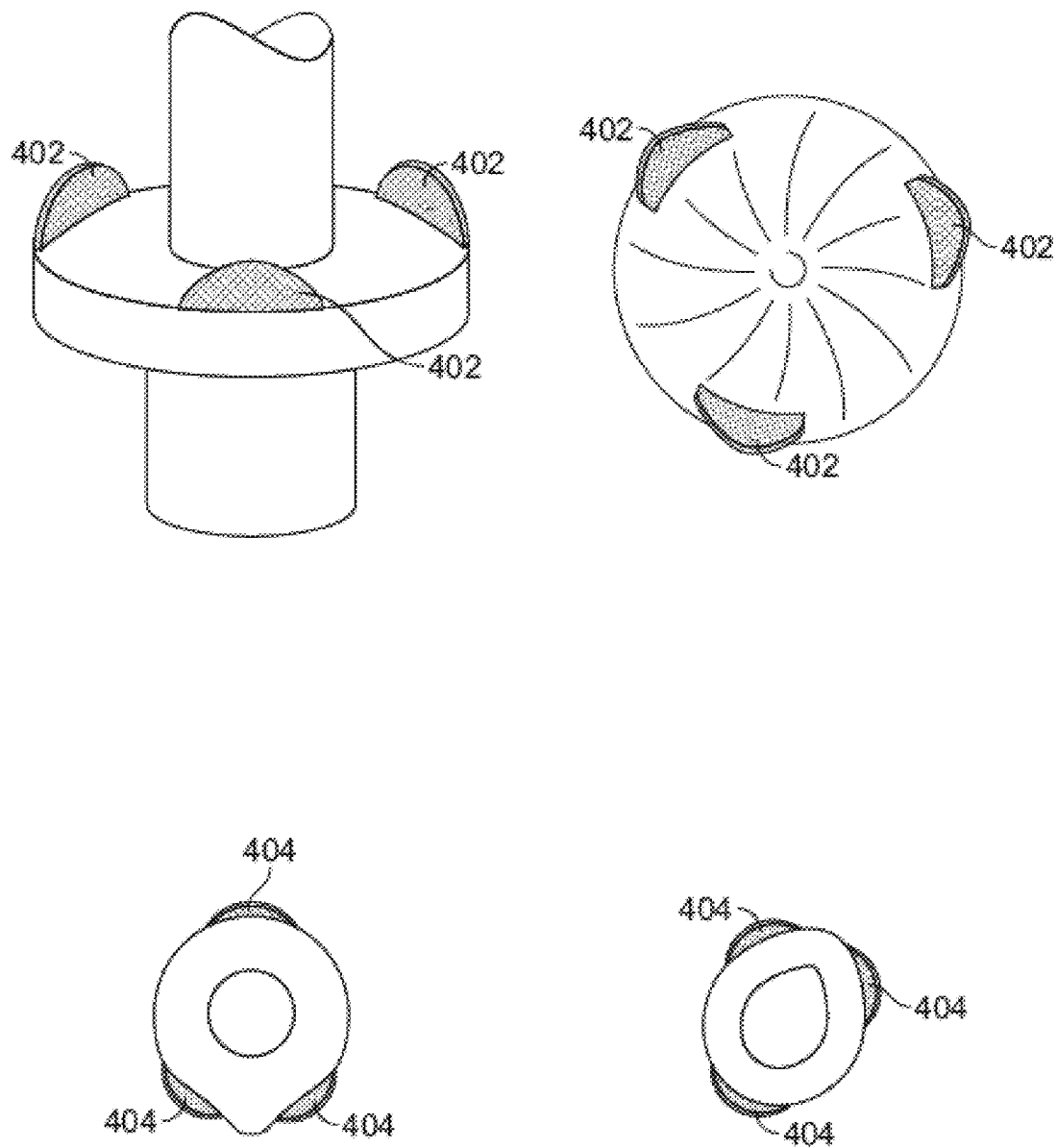
FIG. 5 is a perspective view illustrating an exemplary embodiment of a spindle structure of the orthopaedic fixation assembly.

FIG. 5 may provide a perspective view of an orthopaedic implant illustrating an exemplary embodiment of a spindle to prevent rotation of the implant. In some exemplary embodiments, for example using alignment tabs 402, it may be desirable to control and/or prevent rotation while osseointegration is occurring. The shape, size, number, and position of the porous coated chocks can be matched to the shape of the patient's bone at the planned resection level. The chocks can abut the outer cortex of the bone, stabilize the rotational moments of the spindle, and obviate the need for additional "anti-rotation pins." Alignment tabs 402 may be constructed of titanium, interconnecting porous or "trabecular" metal with or without osteoconductive coating(s) including, but not limited to, hydroxyapatite.

Figure 6:
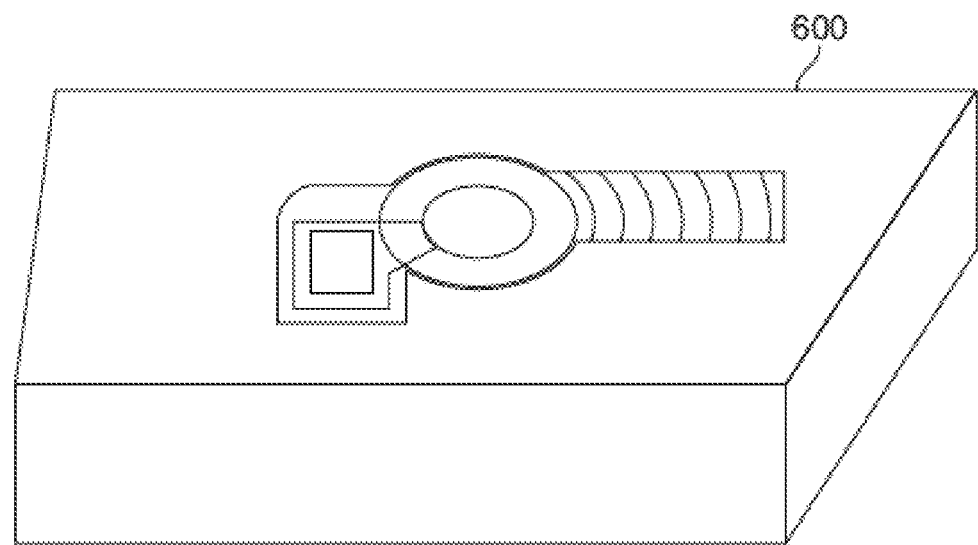
FIG. 6 is a perspective view illustrating a tabletop relief mold for hands-free fabrication of the orthopaedic fixation assembly.

FIG. 6 may illustrate an exemplary embodiment of tabletop relief mold 600 for hands-free assembly of the implant system of the orthopaedic fixation assembly, prior to instrumentation, in the operating room. In the operating room, the assembly and targeting guide 400 may be placed in the holder 600 so that the anchor plug 220 can be inserted within the body cavity 208 of the stem 202 and the end-cap 234 screwed into place, as discussed above in FIGS. 2A and 2B. The relief hold 600 may hold the implant in a predetermined posture, such as in an upright position. This may allow a surgeon to release the anchor plug into the body cavity and securely tighten the end cap to the stem. The relief mold 600 may provide resistance to torque as the end cap is tightened.

The foregoing description and accompanying figures illustrate the principles, preferred embodiments and modes of operation of the invention. However, the invention should not be construed as being limited to the particular embodiments discussed herein. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An orthopaedic fixation assembly adapted to be implanted in a bone of a patient, comprising:
   a main body adapted for insertion into the bone, the main body comprising a longitudinally extending stem, the longitudinally extending stem having a proximal end, a distal end, and a cavity body defining an interior of the longitudinally extending stem between the proximal end and the distal end;
   a spindle structure configured to be attached to the proximal end of the longitudinally extending stem of the main body, the spindle structure comprising a housing configured to interface with an osteotomy surface;

an anchor plug comprising a top portion, a bottom portion, a peripheral side wall and an elongated shaft extending from the bottom portion, the anchor plug configured to be received into the interior of the cavity body and being securable to the longitudinally extending stem; and an end cap configured to secure the anchor plug within the cavity body by engaging with the distal end of the longitudinally extending stem.

2. The orthopaedic fixation assembly of claim 1, wherein the cavity body includes at least one first aperture, the peripheral side wall of the anchor plug includes at least one second aperture, the at least one first aperture and the at least one second aperture being configured to align when the anchor plug is received and secured in the interior of the cavity body.

3. The orthopaedic fixation assembly of claim 1, wherein the spindle structure is fixedly attached to the proximal end.

4. The orthopaedic fixation assembly of claim 1, wherein the spindle structure and the longitudinally extending stem form a unitary element.

5. The orthopaedic fixation assembly of claim 1, wherein:
the end cap is internally threaded and forms a rounded end at the top portion of the longitudinally extending stem when coupled thereto; and
the longitudinally extending stem comprises an external thread disposed on the distal end, the external thread configured to facilitate tightening of the end cap in place.

6. The orthopaedic fixation assembly of claim 1, further comprising:
at least one chock configured to control or prevent rotation of the orthopaedic fixation device, the at least one chock is configured to conform to the shape of the bone.

7. The orthopaedic fixation assembly of claim 6, wherein the at least one chock is configured to abut an outer cortex of the bone.

8. The orthopaedic fixation assembly of claim 1, further comprising:
a porous coating provided at a juncture between the longitudinally extending stem and the spindle structure and interconnecting the longitudinally extending stem and the spindle structure.

9. A system for attaching prosthetic components to a bone, comprising:
an orthopaedic fixation device further comprising:
a main body adapted for insertion into the bone, the main body comprising a longitudinally extending stem, the longitudinally extending stem having a proximal end, a distal end, and a cavity body defining an interior of the longitudinally extending stem between the proximal end and the distal end;
a spindle structure configured to be attached to the proximal end of the longitudinally extending stem of the main body, the spindle structure comprising a housing configured to interface with an osteotomy surface;
an anchor plug comprising a top portion, a bottom portion, a peripheral side wall and an elongated shaft extending from the bottom portion, the anchor plug configured to be received into the interior of the cavity body and being securable to the longitudinally extending stem; and
an end cap configured to secure the anchor plug within the cavity body by engaging with the distal end of the longitudinally extending stem; and a targeting guide configured to engage the spindle structure, the targeting guide having at least one alignment tab configured to provide proper orientation of the spindle structure.

10. The system of claim 9, further comprising:
a traction bar; and
a pedestal configured to hold the traction bar and the anchor plug in a predetermined orientation.

11. The system of claim 10, wherein at least two alignment tabs are configured to be disposed on the spindle structure at a 180-degree interval.

12. The system of claim 11, wherein the pedestal is coupled to or fastened to the targeting guide.

13. An orthopaedic fixation assembly adapted to be implanted in a bone of a patient, comprising:
a main body adapted for insertion into the bone, the main body comprising a longitudinally extending stem, the longitudinally extending stem having a proximal end, a distal end, and a cavity body defining an interior of the longitudinally extending stem between the proximal end and the distal end;
a spindle structure configured to be attached to the proximal end of the longitudinally extending stem of the main body, the spindle structure comprising a housing configured to interface with an osteotomy surface;
an anchor plug comprising a top portion, a bottom portion, a peripheral side wall and an elongated shaft extending from the bottom portion, the anchor plug configured to be received into the interior of the cavity body and being securable to the longitudinally extending stem; and
an end cap configured to secure the anchor plug within the cavity body by engaging with the distal end of the longitudinally extending stem,
wherein the cavity body includes at least one first aperture, the peripheral side wall of the anchor plug includes at least one second aperture, the at least one first aperture and the at least one second aperture being configured to align when the anchor plug is received and secured in the interior of the cavity body.

14. The orthopaedic fixation assembly of claim 13, wherein the spindle structure is fixedly attached to the proximal end.

15. The orthopaedic fixation assembly of claim 13, wherein the spindle structure is fixedly attached to the proximal end.

16. The orthopaedic fixation assembly of claim 13, wherein:
the end cap is internally threaded and forms a rounded end at the top portion of the longitudinally extending stem when coupled thereto; and
the longitudinally extending stem comprises an external thread disposed on the distal end, the external thread configured to facilitate tightening of the end cap in place.

17. The orthopaedic fixation assembly of claim 13, further comprising:
at least one chock configured to control or prevent rotation of the orthopaedic fixation device, the at least one chock is configured to conform to the shape of the bone, wherein the at least one chock is configured to abut an outer cortex of the bone.

18. The orthopaedic fixation assembly of claim 13, further comprising:

a porous coating provided at a juncture between the longitudinally extending stem and the spindle structure and interconnecting the longitudinally extending stem and the spindle structure.

* * * * *